(12) United States Patent
Serhan et al.

(10) Patent No.: US 7,655,010 B2
(45) Date of Patent: Feb. 2, 2010

(54) VERTEBRAL FUSION DEVICE AND METHOD FOR USING SAME

(75) Inventors: Hassan Serhan, South Easton, MA (US); Michael Slivka, Taunton, MA (US); Thomas M. DiMauro, Southboro, MA (US)

(73) Assignee: DePuy Spine, Inc., Raynham, MA (US)

( * ) Notice: Subject to any disclaimer, the term of this patent is extended or adjusted under 35 U.S.C. 154(b) by 359 days.

(21) Appl. No.: 10/675,580

(22) Filed: Sep. 30, 2003

(65) Prior Publication Data

US 2005/0070900 A1    Mar. 31, 2005

(51) Int. Cl.
*A61B 17/60*    (2006.01)
(52) U.S. Cl. ............... 606/90; 606/92; 606/192; 606/249; 623/17.12
(58) Field of Classification Search ........ 606/192, 606/92, 61, 193, 60, 246, 248–249, 279, 606/90; 623/17.11–17.16; 604/509, 48, 604/96.01, 101.02
See application file for complete search history.

(56) References Cited

U.S. PATENT DOCUMENTS

| | | | |
|---|---|---|---|
| 3,875,595 A * | 4/1975 | Froning | 623/17.12 |
| 4,772,287 A | 9/1988 | Ray et al. | |
| 5,015,255 A * | 5/1991 | Kuslich | 128/898 |
| 5,108,404 A * | 4/1992 | Scholten et al. | 606/94 |
| 5,133,755 A | 7/1992 | Brekke | |
| 5,443,514 A | 8/1995 | Steffee | |
| 5,465,711 A * | 11/1995 | Moll et al. | 600/207 |
| 5,549,679 A * | 8/1996 | Kuslich | 623/17.12 |
| 5,562,736 A | 10/1996 | Ray et al. | |
| 5,679,723 A | 10/1997 | Cooper et al. | |

(Continued)

FOREIGN PATENT DOCUMENTS

EP    1 407 730 A1    4/2004

(Continued)

OTHER PUBLICATIONS

Kandziora, Frank, et al., Biomechanical Analysis of Biodegradable Interbody Fusion Cages Augmented With Poly(Propylene Glycol-co-Fumaric Acid), *Spine*, 27(15): 1644-1651 (2002).

(Continued)

*Primary Examiner*—Thomas C Barrett
*Assistant Examiner*—James L. Swiger
(74) *Attorney, Agent, or Firm*—Nutter McClennen & Fish LLP

(57) ABSTRACT

An intervertebral fusion device includes a body having a proximal portion along a major axis of the body and a distal portion along the major axis, and supporting means at the distal portion. The supporting means supports vertebrae in a distracted position while the vertebrae fuse. At least one of the body and the supporting means has a height distinct from a width, whereby the body or supporting means can distract vertebrae, between which the body or the supporting means has been placed, by rotation of the body or the supporting means about the major axis. A method of fusing vertebrae includes the steps of inserting between two vertebrae an intervertebral fusion device and rotating the body or the supporting means, whereby the vertebrae are supported in a distracted position while the vertebrae fuse.

15 Claims, 9 Drawing Sheets

U.S. PATENT DOCUMENTS

| | | | |
|---|---|---|---|
| 5,702,449 A | 12/1997 | McKay | |
| 5,720,726 A * | 2/1998 | Marcadis et al. | 604/103.08 |
| 5,824,084 A | 10/1998 | Muschler | |
| 5,865,845 A | 2/1999 | Thalgott | |
| 5,888,220 A | 3/1999 | Felt et al. | |
| 5,968,098 A | 10/1999 | Winslow | |
| 6,066,154 A * | 5/2000 | Reiley et al. | 606/192 |
| 6,171,610 B1 | 1/2001 | Vacanti et al. | |
| 6,187,048 B1 | 2/2001 | Milner et al. | |
| 6,248,131 B1 | 6/2001 | Felt et al. | |
| 6,258,094 B1 * | 7/2001 | Nicholson et al. | 606/84 |
| 6,280,456 B1 * | 8/2001 | Scribner et al. | 606/192 |
| 6,332,894 B1 | 12/2001 | Stalcup et al. | |
| 6,368,351 B1 | 4/2002 | Glenn et al. | |
| 6,375,655 B1 * | 4/2002 | Zdeblick et al. | 606/61 |
| 6,413,278 B1 * | 7/2002 | Marchosky | 623/17.16 |
| 6,582,446 B1 * | 6/2003 | Marchosky | 606/167 |
| 6,592,625 B2 | 7/2003 | Cauthen | |
| 6,595,998 B2 * | 7/2003 | Johnson et al. | 606/90 |
| 6,679,890 B2 * | 1/2004 | Margulies et al. | 606/94 |
| 6,695,760 B1 * | 2/2004 | Winkler et al. | 600/7 |
| 6,726,691 B2 * | 4/2004 | Osorio et al. | 606/94 |
| 6,752,809 B2 * | 6/2004 | Gorek | 606/92 |
| 2001/0039453 A1 | 11/2001 | Gresser et al. | |
| 2002/0058947 A1 * | 5/2002 | Hochschuler et al. | 606/94 |
| 2003/0009225 A1 | 1/2003 | Khandkar et al. | |
| 2003/0028251 A1 * | 2/2003 | Mathews | 623/17.16 |
| 2004/0073213 A1 * | 4/2004 | Serhan et al. | 606/61 |
| 2004/0102774 A1 * | 5/2004 | Trieu | 606/61 |

FOREIGN PATENT DOCUMENTS

| | | |
|---|---|---|
| FR | 2 764 795 A1 | 12/1998 |
| WO | WO 97/37619 | 10/1997 |
| WO | WO 02/062272 A2 | 8/2002 |

OTHER PUBLICATIONS

Haas, Norbert P., New Products From AO Development [online], May 2002 [retrieved on Oct. 14, 2003]. Retrieved from the Internet <URL: http://www.ao.asif.ch/development/pdf_tk_news_02.pdf>.

Cortek, Inc.: Product Line [online], 2001-2002 [retrieved on Oct. 14, 2003]. Retrieved from the Internet <URL: http://www.cortekinc.com/product.html>.

OSTEOSET® DBM Pellets (Important Medical Information) [online], Nov. 2002 [retrieved on Oct. 14, 2003]. Retrieved from the Internet <URL: http://www.wmt.com/Literature>.

FDA Approves Cambridge Scientific, Inc.'s Orthopedic WISORB™ Malleolar Screw [online], Jul. 30, 2002 [retrieved on Oct. 14, 2003]. Retrieved from the Internet <URL: http://www/cambridgescientificinc.com>.

Australian Examiner's Report from related AU Application No. 2004277963.

European Examiner's Report from related EP Application No. EP20040785211 (Publication No. EP1670398).

International Preliminary Report on Patentability / Written Opinion of the International Searching Authority.

European Examiner's Report from related European Application No. 04785211.6 dated Feb. 16, 2009.

* cited by examiner

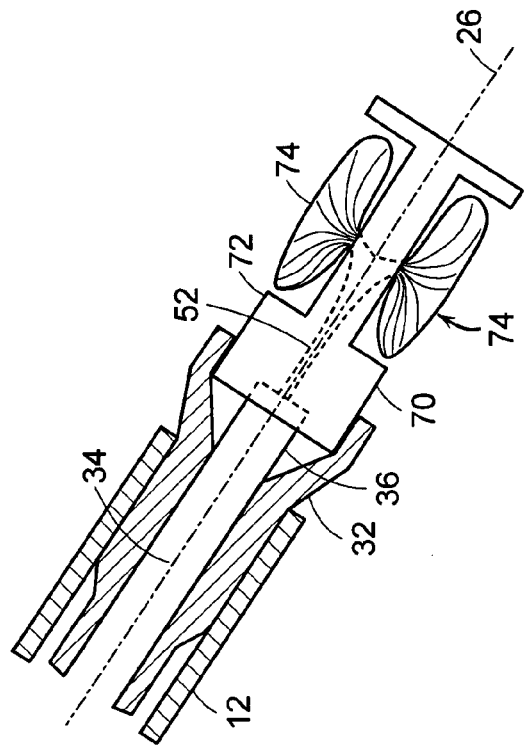
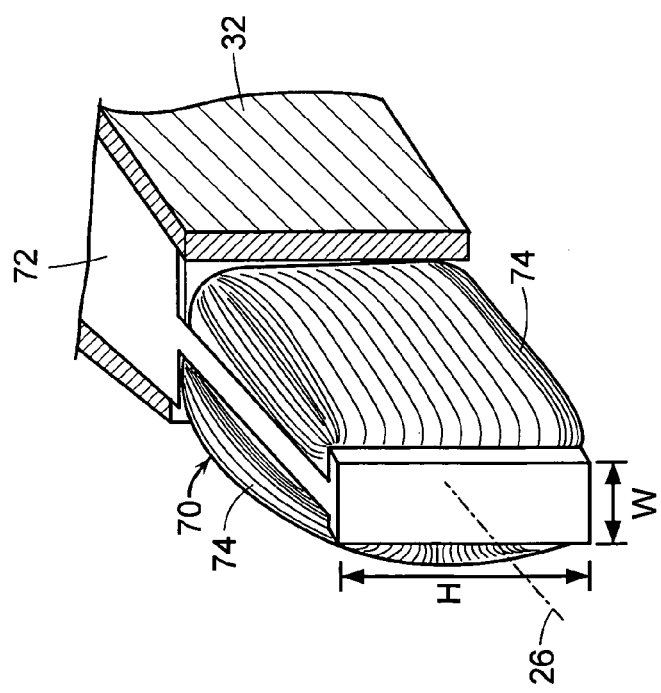

VERTEBRAL FUSION DEVICE AND METHOD FOR USING SAME

BACKGROUND OF THE INVENTION

Spine fusion procedures represent the state of the art treatment for intervertebral disc problems, which generally involve open surgery and the use of interbody fusion cages and spinal fixation systems to stabilize the fusion site.

Less invasive methods of performing interbody fusion have gained popularity in recent years due to deminished disruption of the body's tissues and lower blood loss during surgery, resulting in lower post-operative pain and faster recovery. Anterior lumbar interbody fusion (ALIF) procedures obviate the need to disrupt back muscles and liganients, but requires careful navigation around sensitive structures such as the aorta. Transforaminal lumbar interbody fusion (TLIF) procedures require only one incision made in the patient's back and involves placing a single fusion device obliquely into the disc space. Distraction of the disc space with subsequent decompression of nerve roots can be accomplished by rotating a device between the adjacent vertebrae. However, filling the space around the device with a material, e.g. bone graft, is difficult, time consuming and results in significant morbidity at the graft donor site.

Thus, there is a need for a method and a device that would minimize or overcome the above-referenced problems.

SUMMARY OF THE INVENTION

The present invention relates to a device that can be employed, after performing a discectomy or nucleotomy, to both distract the disc space and inject or insert supporting means into the distracted disc space.

In one embodiment, the present invention is an intervertebral fusion device, comprising (a) a body having a proximal portion along a major axis of the body and a distal portion along the major axis and (b) supporting means at the distal portion that support vertebrae in a distracted position while the vertebrae fuse. The body defines a conduit substantially parallel to the major axis and the supporting means define a conduit in fluid communication with the conduit defined by the body. At least a portion of the body or the supporting means has a height distinct from a width taken along a cross-section of the portion of the body or supporting means perpendicular to the major axis, whereby the portion of the body or supporting means can distract vertebrae, between which the portion of the body or the supporting means has been placed, by rotation of the body or the supporting means about the major axis.

In another embodiment, the present invention is a kit for providing fusion-promoting material comprising an intervertebral fusion device and a flowable osteogenic material selected from the group consisting of morsellized autograft, demineralized bone matrix, bone marrow aspirate, bone marrow concentrate, platelet-rich plasma, hyaluronic acid, collagen, calcium phosphate cements, and bioabsorbable polymers. In another embodiment, the flowable material also contains an added bone growth factor such as a bone morphogenic protein. The device includes (a) a body having a proximal portion along a major axis of the body and a distal portion along the major axis and (b) supporting means at the distal portion that support vertebrae in a distracted position while the vertebrae fuse. The body defines a conduit substantially parallel to the major axis and the supporting means define a conduit in fluid communication with the conduit defined by the body. At least a portion of the body or the supporting means has a height distinct from a width taken along a cross-section of the portion of the body or supporting means perpendicular to the major axis, whereby the portion of the body or supporting means can distract vertebrae, between which the portion of the body or the supporting means has been placed, by rotation of the body or the supporting means about the major axis.

In another embodiment, the present invention is a method of fusing vertebrae, comprising the steps of (a) inserting between two vertebrae an intervertebral fusion device, said device including a body and a supporting means and (b) rotating the body or the supporting means, whereby the vertebrae are supported in a distracted position while the vertebrae fuse, thereby fusing the vertebrae. The body has a proximal portion along a major axis of the body and a distal portion along the major axis and defines a conduit substantially parallel to the major axis. The supporting means at the distal portion of the body supports vertebrae in a distracted position while the vertebrae fuse. The supporting means define a conduit in fluid communication with the conduit defined by the body. At least a portion of the body or the supporting means has a height distinct from a width taken along a cross-section of the portion of the body or supporting means perpendicular to the major axis, whereby the portion of the body or supporting means can distract vertebrae, between which the portion of the body or the supporting means has been placed, by rotation of the body or the supporting means about the major axis.

The present invention has numerous advantages including simultaneous use as a spreader to distract adjacent vertebrae and to surgically implant supporting means. Also, the present invention can substantially restore natural lordosis, kyphosis and/or disk height. The present invention also enables introduction of flowable materials into disk space without subjecting the injected material to compressive forces, thereby permitting the injected material to set, if necessary, prior to applying significant compressive force.

BRIEF DESCRIPTION OF THE DRAWINGS

FIG. 3(a) is a perspective view of another embodiment of a cage of the present invention.

FIG. 3(b) is a plan view of the embodiment of the cage of the present invention shown in FIG. 3(a).

DETAILED DESCRIPTION OF THE INVENTION

Devices of the Invention

Figure 1D:
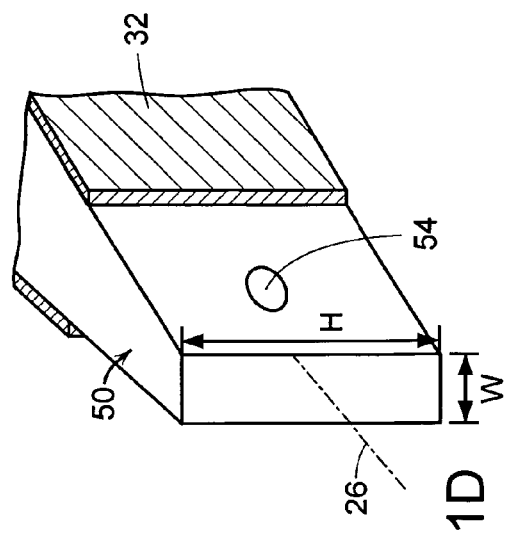
FIG. 1(d) is a perspective view of one embodiment of supporting means of the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The present invention relates to a vertebral fusion device for simultaneously distracting two adjacent vertebral bodies and delivering a flowable material into a disk space. As used herein, the term "vertebral fusion" refers to a medical procedure that results in maintaining separation between vertebrae. In one embodiment, vertebral fusion provides for bony ingrowth that fixes two adjacent vertebrae in a desired, for example, distracted and/or angulated, position.

In a preferred embodiment, a natural angle between two adjacent vertebral plates is replicated by fusing the two adjacent vertebrae. As used herein, the "natural angle" refers either to natural lordosis or to natural kyphosis. In one embodiment, a natural lordosis is replicated or restored. As used herein, the term "natural lordosis" refers to a natural angle between two adjacent vertebral plates within the lumbar or cervical spine segments wherein the distance between the anterior portions of the two adjacent vertebral plates is not smaller than the distance between the posterior portions of the two adjacent vertebral plates. In another embodiment, a natural kyphosis is replicated or restored. As used herein, the term "natural kyphosis" refers to a natural angle between two adjacent vertebral plates within the thoracic spine segment wherein the distance between the anterior portions of the two adjacent vertebral plates is not greater than the distance between the posterior portions of the two adjacent vertebral plates. In another embodiment of vertebral fusion, a fusion means maintains the separation between the vertebrae.

Subsequent to discectomy or nucleotomy, a device of the present invention can be used to distract the adjacent vertebrae, inject a flowable material, for example a fusion-promoting composition, in the intervertebral space and maintain the distracted vertebrae in the distracted position. Additionally, the present invention can be used to at least partially restore natural angle or disk space.

For the purposes of the present invention, the "distal portion" of the device is that portion that penetrates the annulus fibrosis, while the "proximal portion" of the device is that portion that remains outside the annulus fibrosis.

Figure 1B:
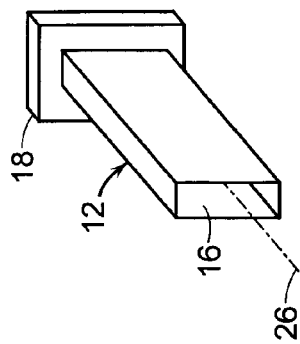
FIG. 1(b) is a perspective view of a cannula of the invention.
Figure 1A:
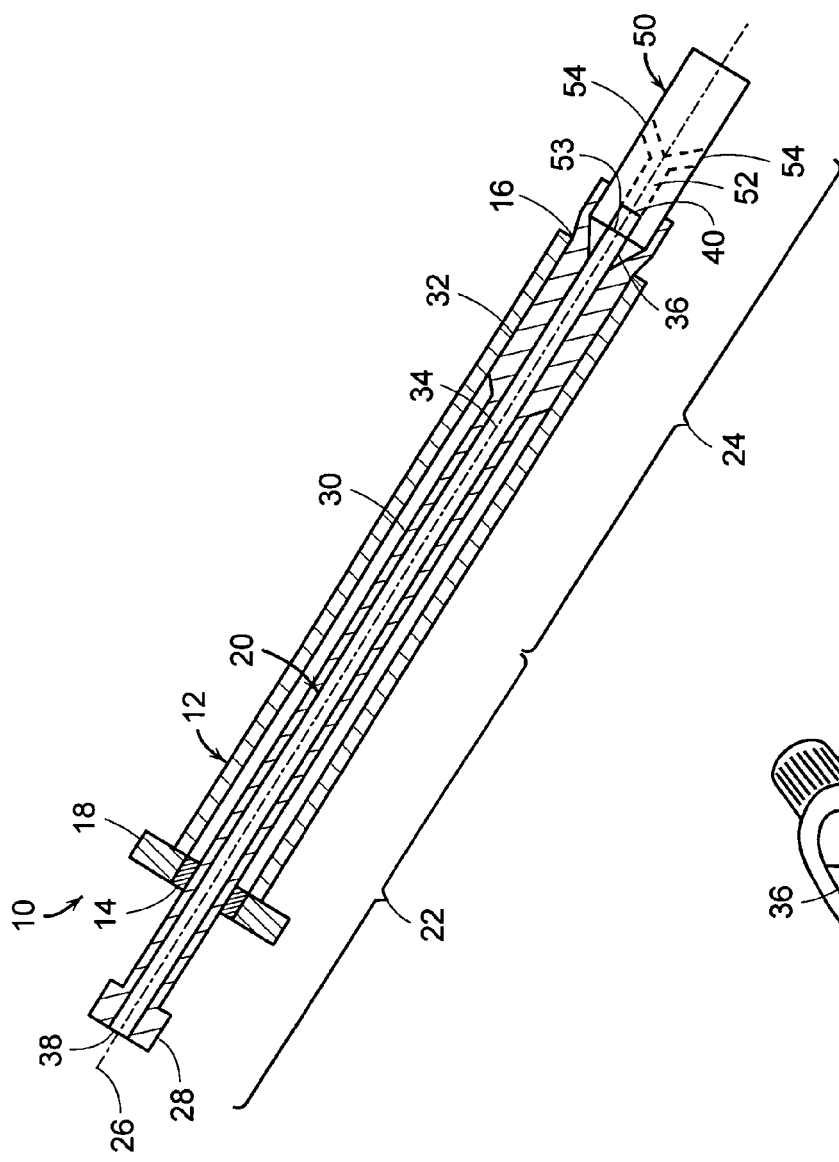
FIG. 1(a) is a plan view of one embodiment of the invention.

Referring to FIG. 1(a), in one embodiment the present invention is an assembly that includes cannula 12 and device 20. Cannula 12 further includes proximal outlet 14, distal outlet 16 and hilt 18. Device 20, having proximal portion 22 and distal portion 24 along major axis 26, includes stopper 28 at proximal portion 22, attached to central section 30 that spans proximal and distal portions 22 and 24 of device 20, clamp 32 at distal portion 24, attached to central section 30 and, preferably, connector 36, attached to clamp 32.

For the purposes of the present invention, the portion of device 20 that includes stopper 28, central section 30, clamp 32 and, preferably, connector 36 is referred to herein as the "body" of the device. The terms "major axis," labeled 26 in FIG. 1(a), and "major axis of the body," are used interchangeably herein.

Device 20 preferably has conduit 34, substantially parallel to major axis 26 and defined by the body of the device. Conduit 34 has inlet 38, located at proximal portion 22 of device 20, preferably in stopper 28, and outlet 40, located at a distal portion of clamp 32 or, preferably, at connector 36.

Figure 1C:
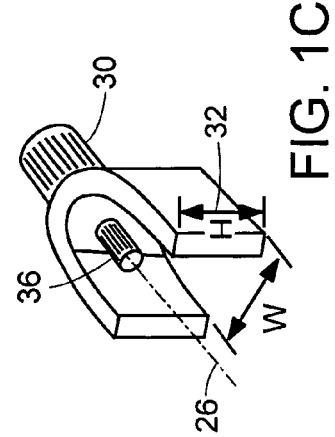
FIG. 1(c) is a perspective view of a clamp portion of the device of the invention.

Cannula 12, shown schematically in FIG. 1(b), preferably has a rectangular cross-section taken perpendicular to major axis 26. Clamp 32 and a distal portion of central section 30 of device 20 are shown in FIG. 1(c). Preferably, central section 30 and connector 36 have circular cross-sections taken perpendicular to major axis 26.

Device 20 further includes supporting means 50 at the distal portion 22 for supporting vertebrae in a distracted position while the vertebrae fuse. Referring to FIG. 1(c) and FIG. 1(d), at least one of the clamp 32 and the supporting means 50 has a height H distinct from a width W taken along a cross-section of clamp 32 or supporting means 50 perpendicular to major axis 26. As the result, clamp 32 or supporting means 50 can distract vertebrae, between which clamp 32 or supporting means 50 has been placed, by rotation of device 20, and thereby clamp 32 or supporting means 50, about major axis 26. Upon placing clamp 32 or supporting means 50 of the present invention between the adjacent vertebrae, a flowable material can be injected through conduit 34 into the disk space.

Figure 1E:
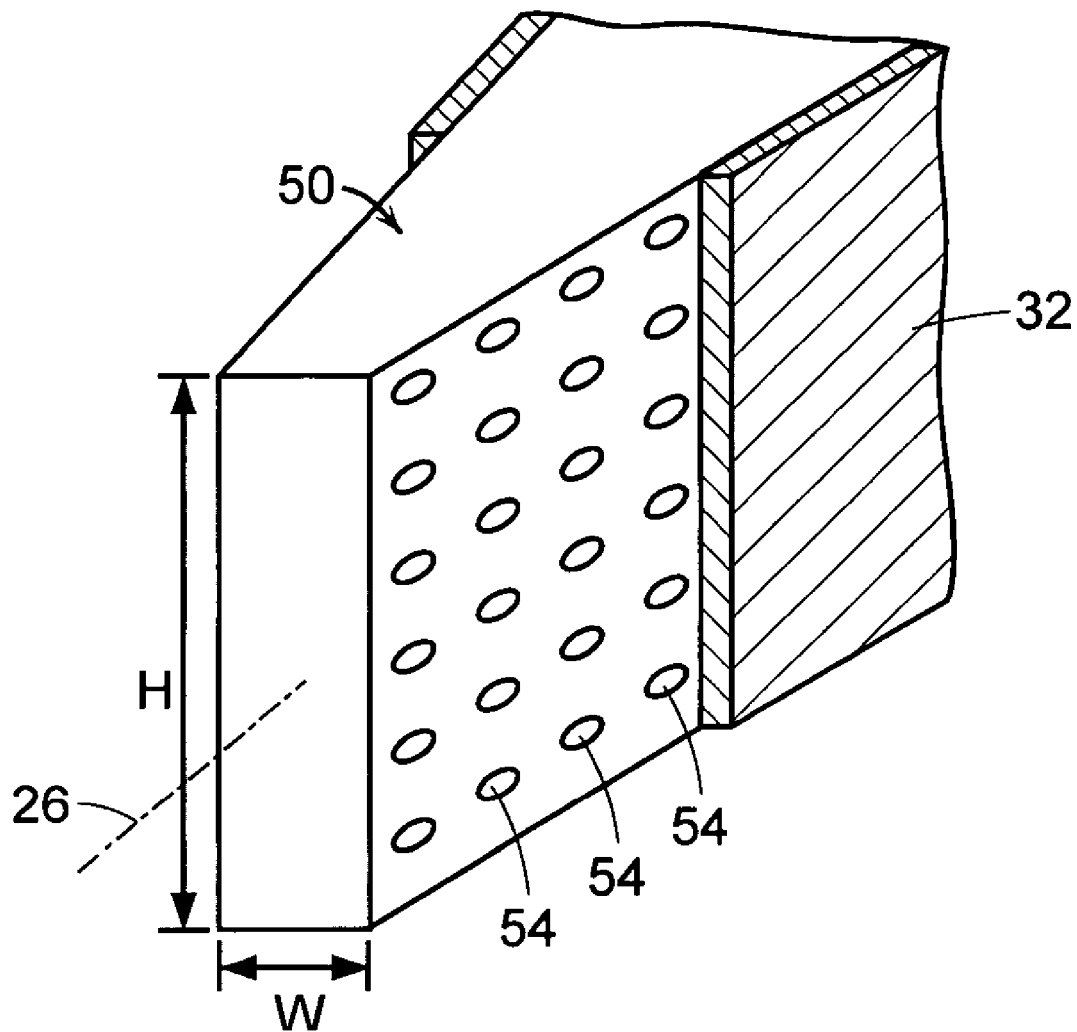
FIG. 1(e) is a perspective view of another embodiment of supporting means of the invention.

Referring to FIG. 1(a), in a preferred embodiment, supporting means 50 includes supporting means conduit 52 having an inlet 53 and at least one outlet 54. Preferably, there are two or more outlets 54. Even more preferably, and now referring to FIG. 1(e), supporting means 50 have multiple outlets 54. Inlet 53 of supporting means conduit 52 is preferably in fluid communication with outlet 40 of conduit 34. In one embodiment, supporting means 50 is an integral part of clamp 32. In a preferred embodiment, supporting means 50 are detachably connected to clamp 32 and connector 36.

In one embodiment, inlet 38 includes a connection means (not shown) to an injection means (not shown). Suitable connection means include a rubber or plastic hose or tube. Suitable injection means include syringe and a pump. Preferably, the injection means is a syringe.

Figure 2A:
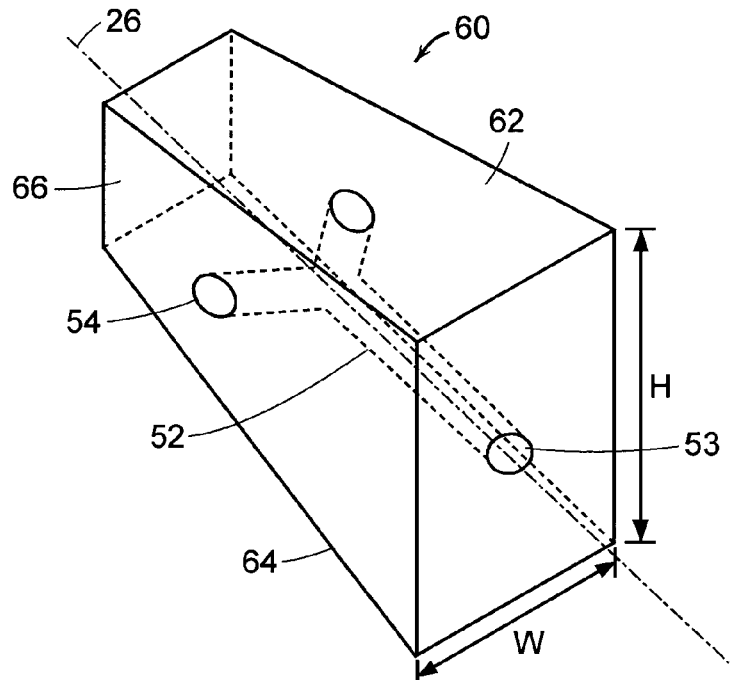
FIG. 2(a) is a perspective view of one embodiment of a cage of the present invention.

In some embodiments, supporting means 50 is selected from the group consisting of a cage, a balloon and a ramp. In a particularly preferred embodiment, the supporting means is a cage 60, depicted in a perspective view in FIG. 2(a) and, as a non-limiting example, in FIGS. 1(a), (d) and (e). Preferably, cage 60 is detachably connected to clamp 32 and, more preferably, to connector 36. In this embodiment, cage 60 defines supporting means conduit 52 that is in fluid communication with conduit 34 defined by the body of device 20. Referring to FIG. 2(a), preferably, cage 60 has a height H distinct from a width W taken along a cross-section of cage 60 perpendicular to major axis 26. As the result, cage 60 can distract vertebrae, between which it has been placed, by rotation of device 20, and thereby cage 60, about major axis 26. Preferably, cage 60 substantially maintains natural angle between the distracted vertebrae. In a particularly preferred embodiment, cage 60 substantially maintains a natural angle between the distracted vertebrae upon detachment of clamp 32 or connector 36 from cage 60.

Figure 2B:
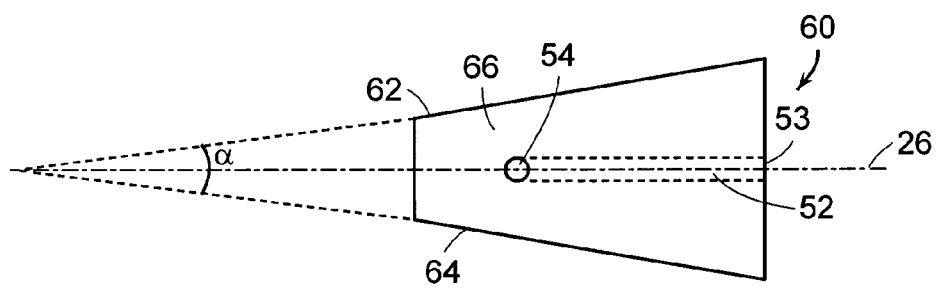
FIG. 2(b) is a lateral view of two embodiments of the cage of the present invention shown in FIG. 2(a).
Figure 2B:
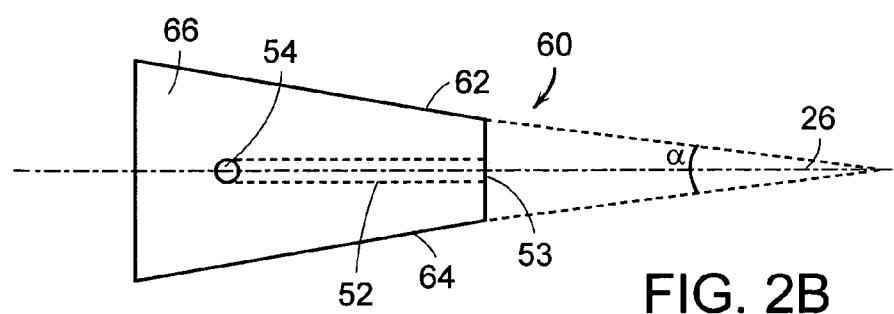

Referring to FIG. 2(b), lateral views of two embodiments of cage 60 are shown. In these embodiments, cage 60 has an upper bearing surface 62, a lower bearing surface 64 and lateral surfaces 66. The upper and lower surfaces define a non-zero angle α, thereby providing an anterior-posterior angle to the distracted disc space. Preferably, the angle α is between about 5 and about 15 degrees. Alternatively, the angle α defined by the upper and the lower bearing surfaces is between about −5 and about −15 degrees. When inserted into the lumbar or cervical spine, the portion of the supporting means having the greater height is preferably facing the anterior side, thus providing lordosis to the spine segment. When inserted into the thoracic spine, the portion of the supporting means having the greater height is preferably facing the posterior side, thus providing kyphosis to the spine segment.

In one preferred embodiment, the supporting member is inserted into the disc space through a transforaminal posterior approach, which causes the device to lie at an angle to the sagittal plane. In this case, the angle, defined by the upper and lower bearing surfaces, is defined along the saggital plane, therefore the supporting member is angled both along the major axis and transversely to the major axis.

Figure 2C:
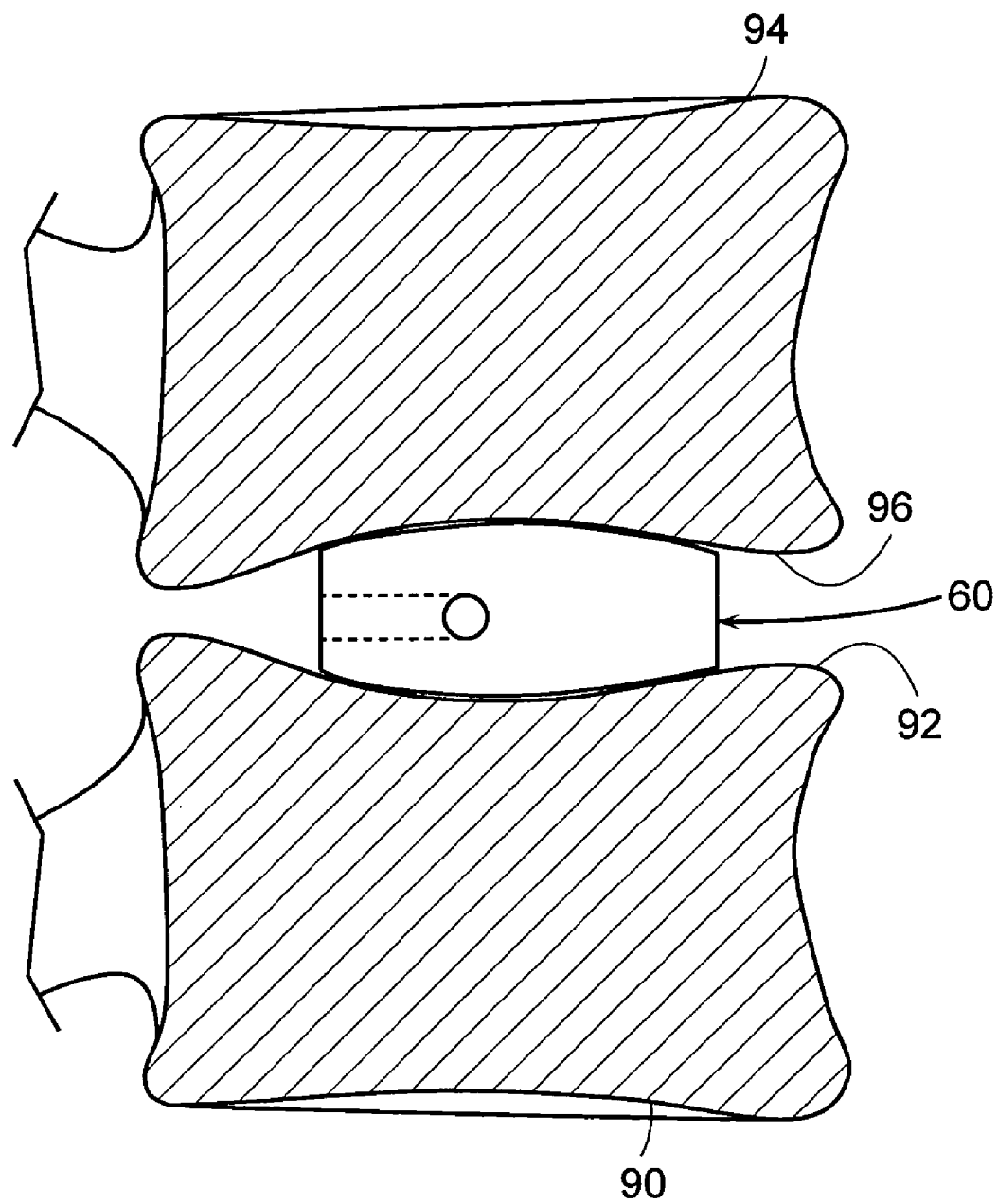
FIG. 2(c) is a lateral view of one embodiment of the cage of the present invention shown in FIG. 2(a).

Referring to FIG. 2(c), in one embodiment, cage 60 has at least one of the bearing surfaces 62 and 64 having a convex shape substantially adapted to match the contour of the vertebral endplates 92 and 94.

In one embodiment, supporting means 50 is cage 70, depicted in perspective view in FIG. 3(a) and, in plan view, in FIG. 3(b). Cage 70 includes frame 72 and at least two expandable balloons 74, connected to frame 72. Cage 70 defines therewithin a supporting means conduit 52. Supporting means conduit 52 is in fluid communication with balloons 74 and with conduit 34 defined by the body of device 20. Preferably, cage 70 is detachably connected to clamp 32 and, more preferably, to connector 36. Preferably, cage 70 has a height H distinct from a width W taken along a cross-section of cage 70 perpendicular to major axis 26. As the result, cage 70 can distract vertebrae, between which it has been placed, by rotation of device 20, and thereby cage 70, about major axis 26. Preferably, cage 70 substantially maintains a natural angle between the distracted vertebrae. In a particularly preferred embodiment, cage 70 substantially maintains a natural angle between the distracted vertebrae upon detachment of clamp 32 or connector 36 from cage 70.

Figure 3C:
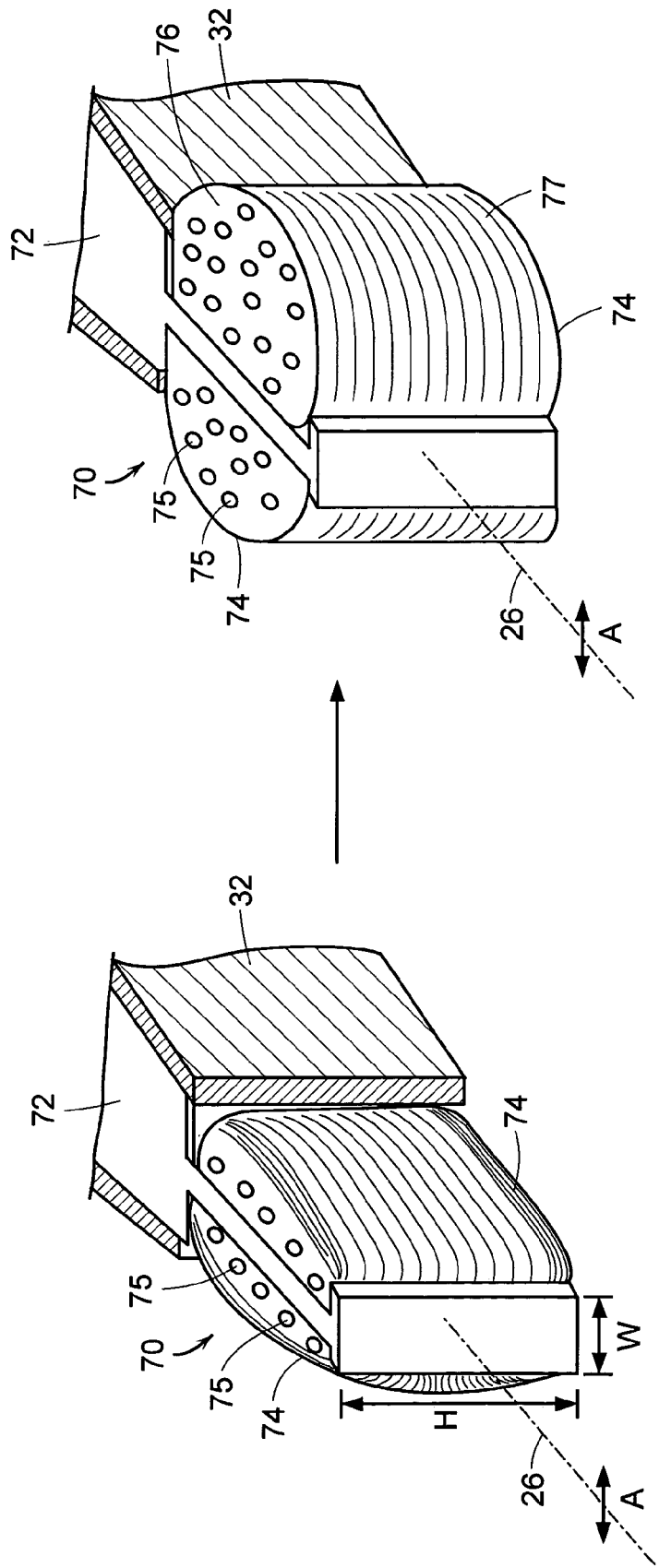
FIG. 3(c) is a perspective view of another embodiment of a cage of the present invention.

In a preferred embodiment depicted in FIG. 3(c), balloons 74 expand substantially in the lateral direction indicated by arrow A. Preferably, balloons 74 have multiple outlets 75 located on upper and lower balloon surfaces 76 and 77. Upon distracting the adjacent vertebrae, a flowable material can be injected through conduit 34 and 52 into balloons 74. The flowable material is allowed to come in contact with the adjacent vertebrae through outlets 75. In this embodiment, the balloon is substantially semi-permeable, whereby leakage outside of the disc space is prevented, while allowing direct contact of the flowable material with the vertebral body endplates.

Figure 4B:
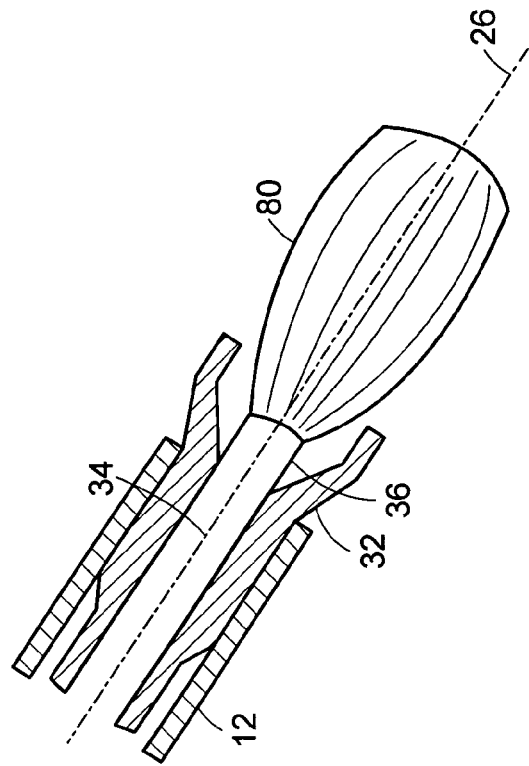
FIG. 4(b) is a plan view of the embodiment of the present invention shown in FIG. 4(a).
Figure 4A:
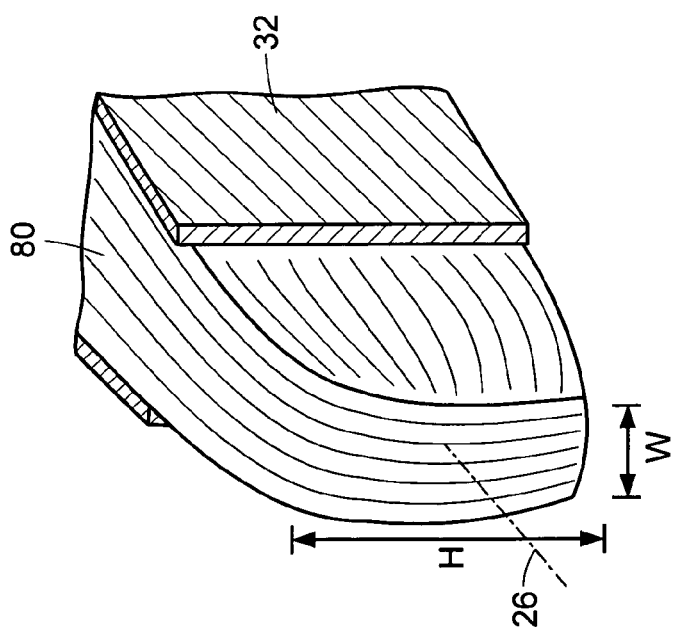
FIG. 4(a) is a perspective view of an embodiment of the present invention wherein a supporting means is a balloon.

In one embodiment, depicted in perspective view in FIG. 4(a) and, in plan view, in FIG. 4(b), supporting means 50 is an expandable balloon 80. Balloon 80 is in fluid communication with conduit 34 defined by the body of device 20. Preferably, balloon 80 is detachably connected to clamp 32 and, more preferably, to connector 36.

Referring to FIG. 4(a), in this embodiment, clamp 32 and balloon 80, subsequent to expansion, have a height H distinct from a width W taken along a cross-section of clamp 32 or balloon 80 perpendicular to major axis 26. As the result, clamp 32 can distract vertebrae, between which clamp 32 has been placed, by rotation of device 20, and thereby clamp 32 about major axis 26. Upon distracting the adjacent vertebrae, a flowable, preferably hardenable, material can be injected through conduit 34 into balloon 80.

In one embodiment, expanded balloon 80 substantially maintains natural angle between the distracted vertebrae. In a preferred embodiment, expanded balloon 80 substantially maintains natural angle between the distracted vertebrae upon detachment of clamp 32 or connector 36 from expanded balloon 80.

Materials Employed by Devices of the Invention

The device can be made of materials typically selected for use in surgical instruments and implants, such as stainless steel, titanium, titanium alloys (Ti-6Al-4V), cobalt-chrome alloys. Preferably, the entire device is sterile.

In one embodiment, the supporting means 50 includes at least one material selected from the group consisting cortical bone graft, bioabsorbable polymer such as poly(lactic acid), poly(glycolic acid), polydioxanone, polyhydroxybutyrate, polyhydroxyvalerate, poly(propylene fumarate), polyoxaesters, amino acid-derived polycarbonates, biodegradable polyurethanes and their copolymers, and non-bioabsorbable polymer such as ether-ketone polymers (polyetheretherketone), poly(ethylene terephthalate), poysulfone, polypropylene, and nylon. These materials may be reinforced with additional materials known in the art, such as carbon fibers, glass fibers, hydroxyapatite fibers or particles.

In one embodiment, the devices of the invention include at least one balloon. In one embodiment, at least one balloon provides relative containment of the flowable material during injection, thereby preventing leakage outside of the disc space. In a preferred embodiment described above, at least one balloon is semi-permeable, thereby preventing leakage outside of the disc space, while allowing direct contact of the flowable material with the vertebral body endplates. In another embodiment, the balloon comprises a biodegradable polymer having a high rate of degradation that would allow the flowable material to contact the vertebral endplates following degradation. Examples include low-molecular weight polymers of lactic and glycolic acid, modified lactic and glycolic acid polymers such as hydroxylated poly(glycolic-co-lactic acid, collagen, and oxidized regenerated cellulose.

In another embodiment, the devices of the invention include at least one balloon that further includes a material selected from the group consisting of polyurethanes, polyolefin copolymers, polyethylene, polycarbonate, polyethylene terephthalate, ether-ketone polymers, woven fibers, non-woven fibers, fabrics and metal mesh.

The devices of the invention can either be made of or include any member of the group consisting of polyetheretherketone (PEEK), polyether block copolymer (PEBAX), acrylonitrile butadiene styrene (ABS), acrylonitrile styrene (ANS), delrin acetal, polyvinyl chloride (PVC), polyethylene napthalate (PEN), polybutylene terephthalate (PBT), polycarbonate, polyetherimide (PEI), polyether sulfone (PES), polyethylene terephthalate (PET), polyethylene terephthalate glycol (PETG), polyamide, aromatic polyamide, polyether, polyester, polymethylmethacrylate, polyurethane copolymer, ethylene vinyl acetate (EVA), ethylene vinyl alcohol, polyethylene, latex rubber, poly tetrafluoroethylene (PTFE), polypropylene, polyolefin, polysiloxane, liquid crystal polymer, ionomer, poly(ethylene-co-methacrylic) acid, silicone rubber, styrene acrylonitrile (SAN), nylon, polyether block amide, thermoplastic elastomer, metal and glass or any combination thereof.

Flowable materials can include a material that hardens into a structure capable of supporting the loads typically experienced by a intervertebral disc. In one embodiment, the flowable material hardens into a porous scaffold into which bone can grow from the surroundings. In another embodiment, the flowable material hardens into a cement that can induce bone growth.

Suitable materials include at least one compound selected from the group consisting of poly(lactic acid) (PLA), poly(glycolic acid), p-dioxanone fibers, polyarylethyl, polymethylmethacrylate, polyurethane, amino-acid-derived polycarbonate, polycaprolactone, aliphatic polyesters, calcium phosphate, unsaturated linear polyesters, vinyl pyrrolidone and polypropylene fumarate diacrylate or mixtures thereof. Additionally, suitable flowable materials can include at least one member selected from the group consisting of mesenchymal stem cells, growth factors, cancellous bone chips, hydroxyapatite, tri-calcium phosphate, polylactic acid polyglycolic acid, polygalactic acid, polycaprolactone, polyethylene oxide, polypropylene oxide, polysulfone, polyethylene, polypropylene, hyaluronic acid, bioglass, gelatin, collagen and chopped polymeric fibers, or mixtures thereof.

Furthermore, suitable flowable materials can include compounds that stimulate and/or support bone growth, such as morsellized autograft, demineralized bone matrix, bone marrow aspirate, bone marrow concentrate, platelet-rich plasma, hyaluronic acid, collagen, calcium phosphate cements, and bioabsorbable polymers. In one embodiment, these compounds include growth factors, differentiation factor and cytokines selected from the group consisting of FGF-1, FGF-2, FGF-4, PDGFs, EGFs, IGFs, PDGF-bb, OP-1, TGF-β, osteoid-inducing factor (OIF), angiogenin(s), endothelins, hepatocyte growth factor and keratinocyte growth factor, osteogenin (BMP-3); BMP-2; OP-1; BMP-2A, -2B, and -7; TGF-β, HBGF-1, HBGF-2; isoforms of platelet-derived growth factors (PDGF), fibroblast growth factors, epithelial growth factors, isoforms of TGF-β, insulin-like growth factors, bone morphogenic proteins, FGF-1 and 4, TGF-β1, TGF-β2, TGF-β3, the bone morphogenetic proteins (BMP's), the growth differentiation factors (GDF's), Indian hedgehog, sonic hedgehog, desert hedgehog, IGF-I, IGF-II, PDGF-AB, PDGF-BB, PDGF-AA; IL-1, IL-2, IL-3, IL-4, IL-5, IL-6, CSF-1, G-CSF, and GM-CSF, or mixtures thereof. The bone growth supporting compounds further include at least one of material selected from the group consisting of mono-calcium phosphate, di-calcium phosphate, octa-calcium phosphate, alpha-tri-calcium phosphate, beta-tri-calcium phosphate, or tetra-calcium phosphate, hydroxyapatite, fluorapatite, calcium sulfate, calcium fluoride, calcium oxide, silicon dioxide, sodium oxide, and phosphorus pentoxide, or mixtures thereof.

A kit for providing a fusion-promoting material comprising the device of the present invention and a flowable material.

Methods of the Invention

In one embodiment, and referring back to FIGS. 1(a) and (b), the present invention is a method of fusing vertebrae.

The method includes a step of inserting between two vertebrae an intervertebral fusion device 20, said device having a proximal portion 22 and distal portion 24 along major axis 26, a stopper 28 at proximal portion 22 connected to a central section 30, that spans proximal and distal portions 22 and 24 of device 20, clamp 32 at distal portion 24, connected to central section 30 and, preferably, connector 36, connected to clamp 32.

For the purposes of the present invention, the portion of device 20 that includes stopper 28, central section 30, clamp 32 and, preferably, connector 36 is referred to herein as the "body" of the device. The terms "major axis," labeled 26 in FIG. 1(a), and "major axis of the body," are used interchangeably herein.

The intervertebral fusion device further includes supporting means 50 at the distal portion 24 for supporting vertebrae in a distracted position while the vertebrae fuse, wherein at least one of clamp 32 and the supporting means 50 has a height H distinct from a width W taken along a cross-section of clamp 32 or supporting means 50 perpendicular to major axis 26, whereby clamp 32 or supporting means 50 can distract vertebrae, between which clamp 32 or supporting means 50 has been placed, by rotation of device 20 or supporting means 50 about the major axis 26 and further wherein the supporting means define a conduit substantially parallel to major axis.

The method further includes the step of rotating device 20 or supporting means 50, whereby the vertebrae are supported in a distracted position while the vertebrae fuse, thereby fusing the vertebrae.

According to the method of the invention, supporting means 50 is inserted between the vertebrae. Preferably, either supporting means 50 or clamp 32 has a height H distinct from a width W taken along a cross-section perpendicular to major axis 26. As the result, rotation of device 20, and thereby of supporting means 50 distracts the vertebrae. Preferably, rotation of device 20, and thereby of supporting means 50 at least partially restores natural angle between the vertebrae.

In a preferred embodiment, at least a portion of an intervertebral disk between said vertebrae is removed resulting in formation of an intervertebral space. The device of the present invention can be used immediately after a discectomy or a nucleotomy. In performing the discectomy or a nucleotomy, the surgeon typically makes a small (~5 mm) hole in the annulus fibrosis through which the nucleus pulposus is removed.

Preferably, the surgeon makes a device entry hole in the annulus fibrosis. The device entry hole is typically made by either making a second hole in the annulus fibrosis larger than the hole through which the nucleotomy is performed or, preferably, by enlarging the hole through which the nucleotomy is performed.

The method of the present invention can further include the step of removing at least a portion of an intervertebral disk between said vertebrae to thereby form an intervertebral space. The intervertebral space can at least partially be filled with at least one member of the group consisting of autologous bone graft, allograft, demineralized bone matrix, tricalcium phosphate granules, bioabsorbable polymer and non-bioabsorbable polymer.

The method of the present invention can further include the step of directing at least one member selected from the group consisting of morsellized autograft, demineralized bone matrix, bone marrow aspirate, bone marrow concentrate, platelet-rich plasma, hyaluronic acid, collagen, calcium phosphate cements, and bioabsorbable polymers, into supporting means conduit 52 defined the supporting means 50. In one embodiment, the flowable material is delivered into the disk space through supporting means conduit 52 and outlets 54. In one embodiment, supporting means 50 is an integral part of clamp 32. In this embodiment, the surgeon preferably allows the material to at least partially cure within the disc space to a point where the at least partially cured material can withstand the compressive forces of the spine without leaking into the spinal canal, then the clamp and supporting means are removed. In another embodiment, supporting means 50 is detachably connected to clamp 32 or connector 36. In this embodiment, the surgeon can remove device 20 from the intervertebral space and leave supporting means in said space.

In a preferred embodiment, either balloons 74 of cage 70 or balloon 80 are filled by directing a flowable material, for example, morsellized autograft, demineralized bone matrix, bone marrow aspirate, bone marrow concentrate, platelet-rich plasma, hyaluronic acid, collagen, calcium phosphate cements, and bioabsorbable polymers through conduit 34 defined by device 20.

In one embodiment, the flowable material is delivered into balloon 80. In one embodiment, the surgeon preferably allows the material to at least partially cure within the disc space to a point where the at least partially cured material can withstand the compressive forces of the spine. At this time, the surgeon can remove device 20 from the patient, leaving supporting means 50 that includes balloon 80 in the intervertebral space.

In another embodiment, the flowable material is delivered into balloons 74 of cage 70. In this embodiment, cage 70 is detachably connected to clamp 32 or connector 36. In this embodiment, the surgeon can remove device 20 from the intervertebral space and leave cage 70 in said space prior to allowing the flowable material to cure.

EXEMPLIFICATION

As a non-limiting example, the deployment of the cage 60 will be illustrated below.

Figure 5A:
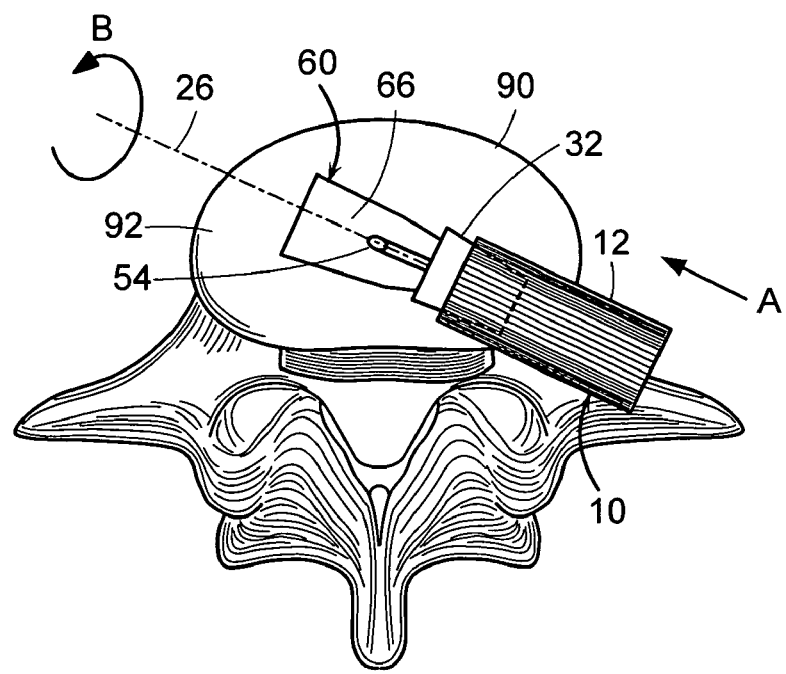
FIG. 5(a) is a plan view depicting the embodiment of the device of the present invention, shown in FIGS. 2(a) and (b), subsequent to the insertion of the device into an intervertebral space.
Figure 5B:
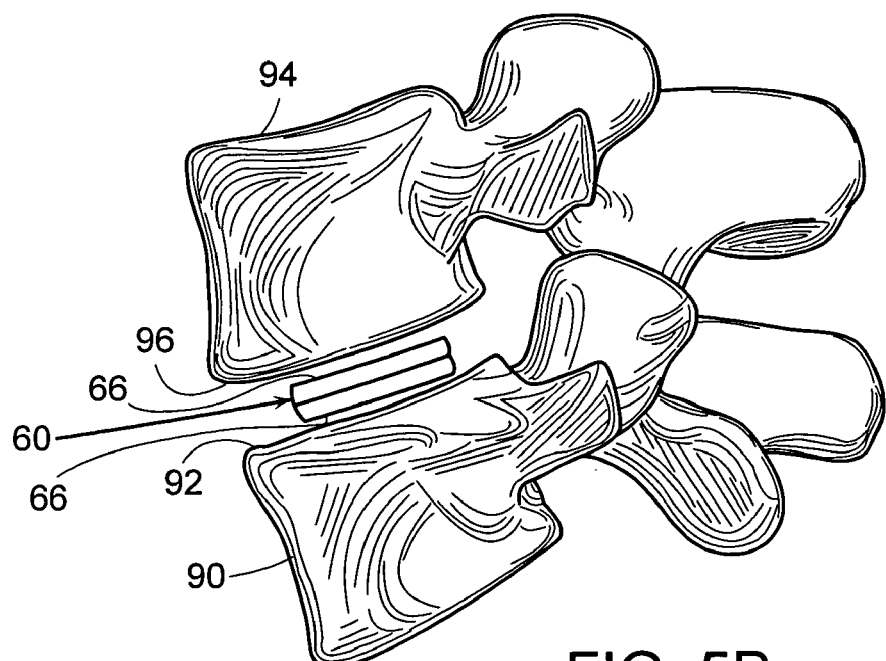
FIG. 5(b) is a lateral view of the embodiment of the device depicted in FIG. 5(a) (only the supporting means are shown).

Referring to FIGS. 5(a) and 5(b), according to the method of the present invention, the surgeon advances assembly 10 through an incision in the annulus fibrosis, and follows by insertion of cage 60 between lower vertebra 90 and the upper vertebra 94 (FIG. 5(b)) in a direction shown by arrow A as depicted in FIG. 5(a). Referring to FIG. 5(b), the initial orientation of cage 60 is such that the lateral surfaces 66 are essentially parallel to lower endplate 92 and upper endplate 96. FIG. 5(b) shows the position assumed by cage 60 in the intervertebral space subsequent to the insertion (for clarity, only cage 60 is shown).

Figure 5C:
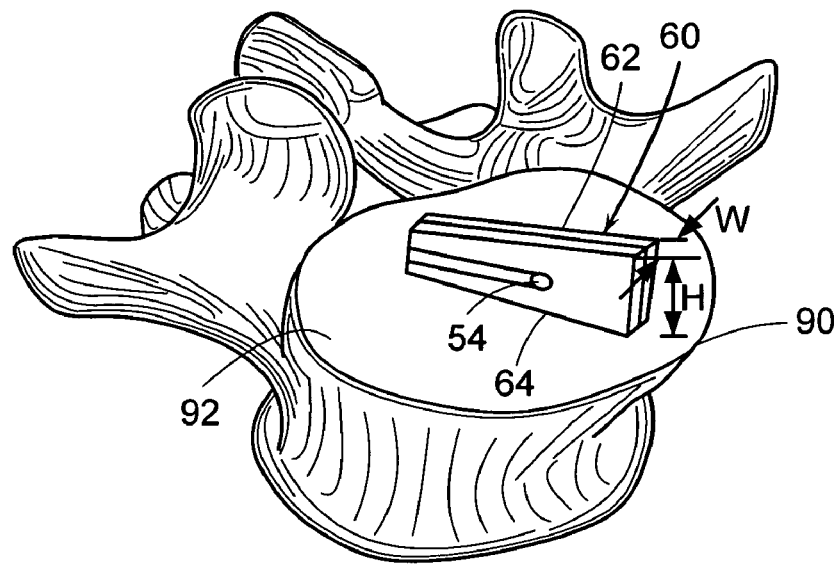
FIG. 5(c) is a perspective view depicting the embodiment of the device of the present invention, as shown in FIGS. 2(a) and (b), subsequent to rotating the device (only the supporting means are shown).
Figure 5D:
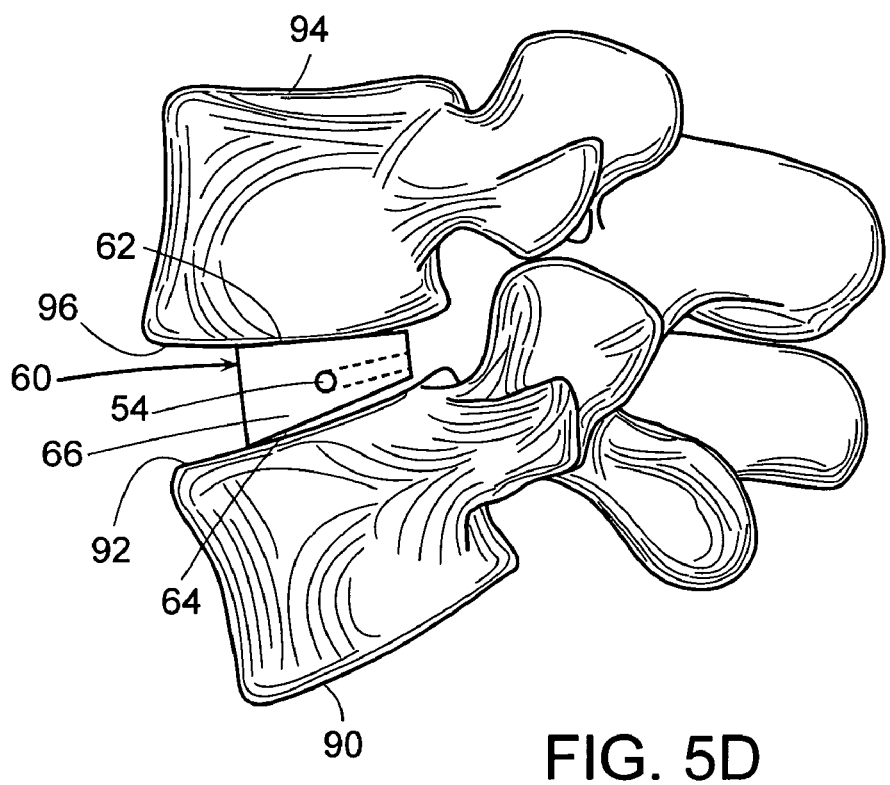
FIG. 5(d) is a lateral view of the embodiment of the device as depicted in FIG. 5(c) (only the supporting means are shown).

Next, now referring to FIGS. 5(c) and 5(d), the surgeon rotates device 20 (not shown), including cage 60, by about 90° (as shown by arrow B in FIG. 5(a)) to the final orientation whereby the bearing surfaces 64 and 62 are in contact with lower endplate 92 and upper endplate 96 (FIG. 5(d)) respectively.

Since, in this example, cage 60 has its height H greater than its width W (see FIG. 5(c)), the rotation achieves the desired distraction of the vertebral bodies 92 and 94.

Next, the intervertebral space (the space between vertebrae 90 and 94) is filled by directing a flowable, fusion-promoting material through conduit 34, supporting means conduit 52 and supporting means conduit outlet 53. The surgeon then allows the material to begin to cure within the disc space to a point where the at least partially cured material can withstand the compressive forces of the spine without leaking into the spinal canal. At this time, the surgeon can remove device 20 and cage 60 from the patient. Alternatively, when using an embodiment of device 20 wherein cage 60 is detachably connected to clamp 32 or connector 36, the surgeon, subsequent to filling the intervertebral space with a flowable, fusion-promoting material, detaches cage 60 from clamp 36 and removes device 20 without cage 60 from the patient. In this embodiment, it is not necessary to allow the material to begin to cure.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. An intervertebral fusion device, comprising:
   (a) a body having a proximal portion along a major axis of the body and a distal portion along the major axis and wherein the body defines a conduit substantially parallel to the major axis, said conduit extending throughout the body; and
   (b) a support at the distal portion that is configured to support vertebrae in a distracted position while the vertebrae fuse and wherein the support includes a conduit in fluid communication with the conduit defined by the body and having at least one outlet on a surface of the support,
   wherein the distal portion of the body is configured to selectively engage the support and at least a portion of the body or the support has a height distinct from a width taken along a cross-section of the portion of the body or support perpendicular to the major axis, whereby the portion of the body or support can distract vertebrae, between which the portion of the body or the support has been placed, by rotation of the body or the support about the major axis.

2. The intervertebral fusion device of claim 1, wherein at least a part of the distal portion of the body has a height distinct from a width taken along the cross-section of the body, whereby the body can distract vertebrae between which at least the part of the distal portion has been placed by rotation of the body about the major axis.

3. The intervertebral fusion device of claim 1, wherein the support is at least one member selected from the group consisting of a cage, a balloon and a ramp.

4. The intervertebral fusion device of claim 1, wherein the support is a cage.

5. The intervertebral fusion device of claim 4, wherein the cage substantially maintains natural angle between the distracted vertebrae.

6. The intervertebral fusion device of claim 4, wherein the cage substantially maintains natural angle between the distracted vertebrae upon detachment of the body from the cage.

7. The intervertebral fusion device of claim 1, wherein the support includes a balloon.

8. The intervertebral fusion device of claim 7, wherein the support further includes at least one material selected from the group consisting of morsellized autograft, demineralized bone matrix, bone marrow aspirate, bone marrow concentrate, platelet-rich plasma, hyaluronic acid, collagen, calcium phosphate cements, and bioabsorbable polymers.

9. The intervertebral fusion device of claim 8, wherein at least one of the morsellized autograft, demineralized bone matrix, bone marrow aspirate, bone marrow concentrate, platelet-rich plasma, hyaluronic acid, collagen, calcium phosphate cements, and bioabsorbable polymers are within the balloon.

10. The intervertebral fusion device of claim 1, wherein the support has a height distinct from a width taken along the cross section of the support, whereby the support can distract vertebrae between which the support has been placed, by rotation of the body and the support about the major axis.

11. The intervertebral fusion device of claim 1, wherein the support is semi-permeable.

12. The intervertebral fusion device of claim 1, wherein the support is biodegradable.

13. A kit for providing a fusion-promoting material comprising:
(a) an intervertebral fusion device, said device including
(i) a body having a proximal portion along a major axis of the body and a distal portion along the major axis and wherein the body defines a conduit substantially parallel to the major axis, said conduit extending throughout the body; and
(ii) a support at the distal portion that is configured to support vertebrae in a distracted position while the vertebrae fuse and wherein the support defines a conduit in fluid communication with the conduit defined by the body and having at least one outlet on a surface of the support, wherein the distal portion of the body is configured to selectively engage the support and at least a portion of the body or the support has a height distinct from a width taken along a cross-section of the portion of the body or support perpendicular to the major axis, whereby the portion of the body or support can distract vertebrae, between which the portion of the body or the support has been placed, by rotation of the body or the support about the major axis; and
(b) a flowable material selected from the group consisting of morsellized autograft, demineralized bone matrix, bone marrow aspirate, bone marrow concentrate, platelet-rich plasma, hyaluronic acid, collagen, calcium phosphate cements, bioabsorbable polymers and bone growth.

14. An intervertebral fusion device, comprising:
(a) a body having a proximal portion along a major axis of the body and a distal portion along the major axis and wherein the body defines a conduit substantially parallel to the major axis, said conduit extending throughout the body, and wherein at least a part of the distal portion of the body has a height distinct from a width taken along a cross-section of the body such that the body can distract vertebrae between which at least a part of the distal portion has been placed by rotation of the body about the major axis; and
(b) a selectively expandable balloon detachably connected to the distal portion of the body, the selectively expandable balloon being configured to support vertebrae in a distracted position while the vertebrae fuse and wherein an inner volume of the expandable balloon is in fluid communication with the conduit defined by the body, the balloon being formed of a biodegradable polymer.

15. The intervertebral fusion device of claim 14, wherein the balloon is formed of a material selected from the group consisting of low-molecule weight polymers of lactic acid, glycolic acid, hydroxylated poly(glycolic-co-lactic) acid, collagen, and oxidized regenerated cellulose.

* * * * *

UNITED STATES PATENT AND TRADEMARK OFFICE
CERTIFICATE OF CORRECTION

PATENT NO. : 7,655,010 B2  Page 1 of 1
APPLICATION NO. : 10/675580
DATED : February 2, 2010
INVENTOR(S) : Serhan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 537 days.

Signed and Sealed this

Twenty-third Day of November, 2010

David J. Kappos
*Director of the United States Patent and Trademark Office*